(12) United States Patent
Yamada et al.

(10) Patent No.: US 7,820,228 B2
(45) Date of Patent: Oct. 26, 2010

(54) MEDICAL DEVICE AND MANUFACTURING METHOD OF COLORED MEDICAL DEVICE

(75) Inventors: Hiroshi Yamada, Otsu (JP); Yosuke Taniguchi, Otsu (JP); Kenji Hioki, Otsu (JP); Chisaka Aoyama, Otsu (JP)

(73) Assignee: I.S.T. Corporation, Otsu-shi (JP)

( * ) Notice: Subject to any disclaimer, the term of this patent is extended or adjusted under 35 U.S.C. 154(b) by 1041 days.

(21) Appl. No.: 11/545,777

(22) Filed: Oct. 11, 2006

(65) Prior Publication Data

US 2008/0078946 A1    Apr. 3, 2008

(30) Foreign Application Priority Data

Oct. 2, 2006    (JP) .............................. 2006-271227

(51) Int. Cl.
*B05D 3/06* (2006.01)
*B29C 71/02* (2006.01)
*G21H 5/00* (2006.01)

(52) U.S. Cl. ...................... 427/2.1; 427/2.23; 427/2.24; 427/542; 427/553; 427/557

(58) Field of Classification Search .................. 427/2.1, 427/2.23
See application file for complete search history.

(56) References Cited

U.S. PATENT DOCUMENTS 4,553,865 A * 11/1985 Ikeda et al. .............. 400/124.1
5,739,779 A * 4/1998 Kunisa et al. ................. 341/59
6,030,371 A * 2/2000 Pursley ........................ 604/527
6,306,105 B1 * 10/2001 Rooney et al. ............... 600/585
2004/0176543 A1 * 9/2004 Asakawa et al. .......... 525/326.3
2006/0073264 A1 * 4/2006 Sakane et al. ................. 427/2.1

FOREIGN PATENT DOCUMENTS

| JP | 3-267977 A | 11/1991 |
|---|---|---|
| JP | 2003-250905 | 9/2003 |
| JP | 2004-130123 | 4/2004 |
| JP | 2004177780 A * | 6/2004 |

OTHER PUBLICATIONS

Powder coatings. Powder Coating Institute. Retrieved from http://www.p2pays.org/ref/10/09791.pdf. Dec. 16, 2005.*

* cited by examiner

*Primary Examiner*—Timothy H Meeks
*Assistant Examiner*—Cachet I Sellman
(74) *Attorney, Agent, or Firm*—Global IP Counselors, LLP

(57) ABSTRACT

A method for the manufacture of a medical wire includes manufacturing a fluororesin-coated wire and irradiating with infrared radiation. The fluororesin-coated wire is manufactured with a fluororesin-containing liquid, or fluororesin powder body being applied to the outer circumference of a superelastic alloy wire or of a resin-coated superelastic alloy wire. The fluororesin-coated wire is irradiated with a defined wavelength of infrared radiation for a defined period of time.

8 Claims, No Drawings

MEDICAL DEVICE AND MANUFACTURING METHOD OF COLORED MEDICAL DEVICE

FIELD OF THE INVENTION

The present invention relates to a method for manufacturing a medical wire and a colored medical device.

BACKGROUND OF THE INVENTION

In the past, techniques have been proposed such as coating a fluororesin onto a superelastic alloy wire of Ni—Ti or the like to improve the sliding characteristics of a medical wire, or using a pigment-containing fluororesin as the outermost layer of a medical wire so that physicians and the like in a treatment facility are able to identify the appropriate medical wire using only the external appearance (for example, see Japanese Published Unexamined Patent Application No. 2003-250905).

Usually in such cases, a fluororesin will exhibit superior properties only after it is baked at a temperature at or above its melting point (usually 350-400° C.). For this reason, medical guide wires coated with a fluororesin (referred to below as fluororesin-coated medical guide wires) are subjected to a final baking treatment for a period of about 1 minute in an air-circulating oven or the like where the temperature is increased to be at or above the melting point of the fluororesin (for example, see Japanese Published Unexamined Patent Application No. 2004-130123).

SUMMARY OF THE INVENTION

Problem Solved by the Invention

However, such a method has a problem in that the elastic modulus of the superelastic alloy wire is somewhat impaired when the fluororesin-coated medical guide wire is baked (however, this is not a problem in practice). Moreover, when the fluororesin-coated medical guide wire is baked, if the fluororesin contains a coloring substance such as a pigment, there will be a problem if the color of the pigment contained in the fluororesin ends up fading and cannot produce the desired color.

The subject of the present invention is to offer a method for the manufacture of a medical wire that can elicit the superior qualities of a fluororesin while sustaining the elastic modulus of the superelastic alloy wire. In addition, another object of the present invention is to offer a method for the manufacture of a colored medical device that can elicit the superior qualities of a fluororesin while maintaining the color of the pigment contained in the fluororesin.

Means to Solve the Problem

The method for manufacturing the medical wire that relates to the present invention is provided with a process for manufacturing a fluororesin-coated wire and a process for irradiating with infrared radiation. In the process for manufacturing the fluororesin-coated wire, the fluororesin-coated wire is manufactured with a fluororesin-containing liquid or a fluororesin powder body being applied to the outer circumference of a superelastic alloy wire or synthetic resin-coated superelastic alloy wire. Furthermore, synthetic resin-coated superelastic alloy wire as used here is a superelastic alloy wire that is coated with a synthetic resin. In addition, synthetic resin as used here is a resin other than a resin containing fluororesin only (that would correspond to a synthetic resin that has a partial fluororesin). Moreover, fluororesin-containing liquid as used here is a liquid that contains fluororesin. In the process for irradiating with infrared radiation, the fluororesin-coated wire is irradiated with a defined wavelength of infrared radiation for a defined period of time. Furthermore, defined wavelength as used here is preferably a wavelength of 0.9-5.6 μm (micrometer). Additionally, defined period of time as used here is preferably 3-20 seconds. Further preferred is 5-10 seconds.

The reasons why the abovementioned manufacturing method maintains the elastic modulus of a superelastic alloy wire are considered below.

With a circulating hot air oven (thermostatic oven) being used for baking the fluororesin, the fluororesin coated onto the outer circumference of a superelastic alloy wire is provided with heat energy through contact of the surface with hot air, and when it is heated to the melting temperature or above, it will melt, which is considered to constitute the baking process. For this reason, since it takes a relatively long period of time for the fluororesin surface to reach the fluororesin melting point or higher, the heat energy is thought to be transmitted to the interior during this period. Consequently, when the fluororesin is baked in a circulating hot air oven, it becomes more difficult to protect the superelastic alloy wire in the interior from the heat energy.

At the same time, with heating that is due to light energy or electromagnetic wave energy, an energy transfer medium such as air is unnecessary, and a substance can be heated directly by light or electromagnetic radiation. For example, when using near infrared radiation, it is possible to heat the fluororesin in the vicinity of the surface up to the temperature of 400° C. for only 1-3 seconds. In addition, a quartz heater that is a typical infrared radiative heater that can irradiate infrared radiation of the middle infrared radiation region can heat itself, and can also increase the level of the ambient temperature of the surroundings. In other words, if a quartz heater is used, when the ambient temperature can be regulated in the vicinity of from 200° C. to 300° C. that is at or below the allowable temperature limit for the superelastic alloy wire, the object will be irradiated with middle infrared radiation in the vicinity of 1.5-2.0 μm at the ambient temperature. For this reason, if a quartz heater is used, it will exert practically no effect on the superelasticity of the superelastic alloy wire, and the fluororesin in the vicinity of the surface is considered to be able to reach the fluororesin melting point for a short period of time.

Moreover, the method for the manufacture of a colored medical device that relates to the present invention is provided with a process for manufacturing a colored medical device substrate and a process for irradiating with infrared radiation. Furthermore, medical device as used here is a guide wire or catheter or the like. In the process for manufacturing a colored medical device substrate, the colored medical device substrate is manufactured by a colored fluororesin-containing liquid or fluororesin powder body that contains a coloring substance being applied to the external surface of a medical device substrate. Furthermore, colored fluororesin-containing liquid as used here is a liquid that contains a fluororesin and a coloring substance. In addition, coloring substance as used here is a pigment or dye or the like. In the process for irradiating with infrared radiation, a colored medical device substrate is irradiated with a defined wavelength of infrared radiation for a defined amount of time. Furthermore, defined wavelength as used here is preferably a wavelength of 0.9-5.6 μm (micrometer). Additionally, defined period of time as used here is preferably 3-20 seconds. Further preferred is 5-10 seconds.

Moreover, the method for the manufacture of a fluororesin-coated colored medical device relating to the present invention is provided with a process for manufacturing a colored medical device substrate, a process for manufacturing a fluororesin-coated colored medical device substrate, and a process for irradiating with infrared radiation. In the process for manufacturing a colored medical device substrate, the colored medical device substrate is manufactured by a colored fluororesin-containing primer liquid being applied to the outer surface of the medical device substrate. Furthermore, colored fluororesin-containing primer liquid as used here is a primer liquid that contains fluororesin and a coloring substance. In the process for manufacturing a fluororesin-coated colored medical device substrate, a fluororesin-coated colored medical device substrate is manufactured by a fluororesin-containing liquid or fluororesin powder body that does not contain a coloring substance being applied to the external surface of a colored medical device substrate. Furthermore, fluororesin-containing liquid as used here is a liquid that contains fluororesin and does not contain a coloring substance. In the process for irradiating with infrared radiation, a fluororesin-coated colored medical device substrate is irradiated with a defined wavelength of infrared radiation for a defined period of time. If the method for manufacturing a fluororesin-coated colored medical device relating to the present invention is used, the color of the coloring substance can be maintained while the fluororesin is baked sufficiently, and the sliding characteristics of the colored medical device can be maintained at a high level.

In addition, the method for manufacturing a colored medical device relating to the present invention is provided with a process for manufacturing a first colored medical device substrate, a process for manufacturing a second colored medical device substrate, and a process for irradiating with infrared radiation. In the process for manufacturing a first colored medical device substrate, the first colored medical device substrate is manufactured by a colored fluororesin-containing primer liquid being applied to the outer surface of the medical device substrate. Furthermore, colored fluororesin-containing primer liquid as used here is a primer liquid that contains fluororesin and coloring substance. In the process for manufacturing a second colored medical device substrate, the second colored medical device substrate is manufactured by a colored fluororesin-containing liquid or fluororesin powder body that contains a coloring substance being applied to the external surface of the first colored medical device substrate. Furthermore, colored fluororesin-containing liquid as used here is a liquid that contains a fluororesin and a coloring substance. In the process for irradiating with infrared radiation, a second colored medical device substrate is irradiated with a defined wavelength of infrared radiation for a defined period of time. If the method for manufacturing a colored medical device relating to the present invention is used, the color of the coloring substance can be maintained while the fluororesin is baked sufficiently, and the color of interest can be more easily brought out.

The reasons why the abovementioned manufacturing method maintains the freshness of the color of the coloring substance are considered below.

With a circulating hot air oven (thermostatic oven) being used for baking the fluororesin, the fluororesin that is coated onto the outer surface of a medical device substrate is provided with heat energy through contact of the surface with hot air, and when it is heated to the melting temperature or above it melts, which is considered to constitute the baking process. For this reason, since it takes a relatively long period of time for the fluororesin surface to reach the melting point or higher, it is thought that the heat energy will be substantially transmitted to the coloring substance over this period. Consequently, when the fluororesin is baked in a circulating hot air oven, it becomes more difficult to protect the coloring substance that is contained in the fluororesin from the heat energy.

At the same time, in heating due to light energy or electromagnetic wave energy, an energy transfer medium such as air is unnecessary, and a substance can be heated directly by light or electromagnetic radiation. For example, when using near infrared radiation, it is possible to heat the fluororesin in the vicinity of the surface up to the temperature of 400° C. for only 1-3 seconds. In addition, a quartz heater that is a typical infrared radiative heater that can irradiate infrared radiation of the middle infrared radiation region can heat itself, and can also increase the level of the ambient temperature of the surroundings. In other words, if a quartz heater is used, when the ambient temperature can be regulated in the vicinity of from 200° C. to 300° C. that is at or below the allowable temperature limit for the coloring substance, the object will be irradiated with middle infrared radiation in the vicinity of 1.5-2.0 μm at the ambient temperature. For this reason, if a quartz heater is used, the fluororesin in the vicinity of the surface can reach the fluororesin melting point for a short period of time, and the baking treatment can be completed within a short period of time. Consequently, it is thought that the fluororesin can be baked while practically no effect will be exerted on the color of the coloring substance.

Furthermore, if the colored medical device substrate is a superelastic alloy wire or a superelastic alloy wire coated with a synthetic resin (excluding a synthetic resin containing fluororesin only), use of the manufacturing method relating to the present invention can maintain the elastic modulus of the superelastic alloy wire. The reasons why the abovementioned manufacturing method maintains the elastic modulus of a superelastic alloy wire are considered below.

With a circulating hot air oven (thermostatic oven) being used for baking the fluororesin, the fluororesin that is coated onto the outer circumference of a superelastic alloy wire is provided with heat energy through contact of the surface with hot air, and when it is heated to the melting temperature or above it melts, which is considered to constitute the baking process. For this reason, since it takes a relatively long period of time for the fluororesin surface to reach the melting point or higher, the heat energy is thought to be transmitted to the interior over this period. Consequently, when the fluororesin is baked in a circulating hot air oven, it becomes more difficult to protect the superelastic alloy wire in the interior from the heat energy.

At the same time, with heating due to light energy or electromagnetic wave energy, an energy transfer medium such as air is unnecessary, and a substance can be heated directly by the light or electromagnetic radiation. For example, when using near infrared radiation, it is possible to heat the fluororesin in the vicinity of the surface up to the temperature of 400° C. for only 1-3 seconds. In addition, a quartz heater that is a typical infrared radiative heater that can irradiate infrared radiation of the middle infrared radiation region can heat itself, and can also increase the level of the ambient temperature of the surroundings. In other words, if a quartz heater is used, when the ambient temperature can be regulated in the vicinity of from 200° C. to 300° C. which is at or below the allowable temperature limit for the superelastic alloy wire, [the object] is irradiated with middle infrared radiation in the vicinity of 1.5-2.0 μm at ambient temperature. For this reason, if a quartz heater is used, it will exert practically no effect on the superelasticity of the superelastic alloy wire, and the fluororesin in the vicinity of the surface is thought to be able to reach the fluororesin melting point for a short period of time.

Effect of the Invention

The inventors of the present application, from the results of carefully repeated experiments and examination, discovered that by irradiating a fluororesin-coated wire with infrared radiation of 0.9-5.6 μm for 3-20 seconds, the fluororesin is baked sufficiently without any impairment of the elastic modulus of the superelastic alloy wire and the fluororesin could be baked sufficiently while maintaining the color of the coloring substance. Consequently, according to the method for the manufacture a medical wire relating to the present invention, the superior properties of the fluororesin can be elicited without any impairment of the elastic modulus of the superelastic alloy wire. Additionally, according to the method for the manufacture of a medical wire relating to the present invention, the superior properties of the fluororesin can be elicited without any fading of the color of the coloring substance. Furthermore, in the method for the manufacture of a medical wire and the method for the manufacture of a colored medical device of the present invention, the time period for baking the fluororesin is substantially shortened when compared to conventional methods. Consequently, according to the method for the manufacture a medical wire and the method for the manufacture of a colored medical device relating to the present invention, the costs for manufacturing a medical wire that is coated with fluororesin and for a colored medical device will be substantially reduced.

DETAILED DESCRIPTION OF THE INVENTION

Method for Manufacturing a Wire in Accordance with the Present Invention

A method for manufacturing a wire that relates to an embodiment of the present invention is chiefly constituted from a primer application process, a colored fluororesin coating process and a colored fluororesin baking process. Moreover, the raw materials that are necessary in this method for manufacturing a wire are chiefly a superelastic alloy wire, primer, fluororesin and a coloring substance.

Below, after the necessary raw materials for implementing the present manufacturing method are mentioned, each process in the present manufacturing method will be described in detail.

Raw Materials (1) Superelastic Alloy Wire

For the superelastic alloy wire that is utilized in an embodiment of the present invention, either a straight shape or a fine-pointed taper shape is preferred. Examples of the superelastic alloy that can be named include Ni—Ti (Ni: 49-51 atom %, including a third element added to Ni—Ti), Cu—Al—Zn (Al: 3-8 atom %; Zn: 15-28 atom %), Fe—Mn—Si (Mn: 30 atom %, Si: 5 atom %), Cu—Al—Ni (Ni: 3-5 atom %, Al: 28-29 atom %), Ni—Al (Al: 36-38 atom %), Mn—Cu (Cu: 5-35 atom %), Au—Cd (Cd: 46-50 atom %) and the like. Furthermore, this superelastic alloy is also known as a shape-memory alloy. In the present invention, the Ni—Ti alloy is preferred. It is preferable for the size of the superelastic alloy wire to be selected by considering the inner diameter of the catheter with which it is to be used and a flexibility that is suitable for this use. In concrete terms, it is desirable to use a superelastic alloy wire with a diameter on the order of approx. 0.3-1 mm.

Furthermore, as the superelastic alloy wire in the present embodiment, it is also desirable to use a superelastic alloy wire that is coated with a synthetic resin (referred to below as a synthetic resin-coated superelastic alloy wire). Further, examples of the synthetic resin that can be named include common synthetic resins such as polyamide resin such as nylon, poly(vinyl chloride) resin, polypropylene resin, epoxy resin, poly(phenylene sulfide) resin, polyether sulfone resin, polyether ketone resin, polysulfone resin, polyamideimide resin, polyether amide resin, polyimide resin, silicone rubber, polyurethane resin and blends of the foregoing.

(2) Primer

The primer in the present embodiment is the solution of a resin with superior adhesive properties with respect to the superelastic alloy wire or a precursor of such a resin containing a fluororesin. Examples of resins that have superior adhesive properties with respect to the superelastic alloy wire include acrylic resin, epoxy resin as well as blends of the foregoing. Examples of the fluororesin that can be named include poly(tetrafluoroethylene) (PTFE), tetrafluoroethylene-perfluoroalkylvinyl ether copolymer (PFA), tetrafluoroethylene-hexafluoropropylene copolymer (FEP), poly(chlorotrifluoroethylene) (PCTFE), poly(vinylidene fluoride) (PVDF), poly(vinyl fluoride) (PVF) as well as tetrafluoroethylene-ethylene copolymer (PETFE) or blends of the foregoing.

(3) Fluororesin

The fluororesin is preferably at least one fluororesin selected from the group consisting of poly(tetrafluoroethylene) (PTFE), tetrafluoroethylene-perfluoroalkylvinyl ether copolymer (PFA), poly(chlorotrifluoroethylene) (PCTFE), poly(vinylidene fluoride) (PVDF), poly(vinyl fluoride) (PVF), tetrafluoroethylene-hexafluoropropylene copolymer (FEP) or tetrafluoroethylene-ethylene copolymer (PETFE). Fluororesin is stable and inert, since it must be safe even when it comes into contact with blood when introduced into the body.

Furthermore, in the method for manufacturing the medical wire of the present embodiment, a dispersion or powder body form of the fluororesin can also be used.

(4) Pigment

For the pigment, it is preferable to select at least one pigment selected from the group consisting of inorganic white pigments such as zinc oxide (zinc white), lead white (silver white), lithopone (pigment mixture of zinc oxide and zinc sulfide), titanium dioxide (titanium white), ceramic white and the like, inorganic extender pigments such as precipitated barium sulfate and barite powder, inorganic red pigments such as red lead, Bengal red (red iron oxide), cadmium red, vermillion and the like, inorganic orange pigments such as cadmium orange, chrome vermillion and the like, inorganic yellow pigments such as yellow lead (chrome yellow), yellow zinc (zinc chromate, zinc yellow), cadmium yellow, yellow ochre, nickel titanium yellow, bismuth vanadium yellow and the like, inorganic brown pigments such as sienna earth, amber earth, Vandyke brown and the like, inorganic blue pigments such as ultramarine blue, iron blue (Prussian blue), cobalt blue, cerulean blue, manganese blue and the like, inorganic green pigments such as viridian, chrome oxide green, cobalt green and the like, inorganic purple pigments such as cobalt violet, manganese violet and the like, inorganic black pigments such as ivory black, peach black, lamp black, Mars black, compound oxide black, carbon black and the like, organic red pigments such as alizarin red, quinacridone red, naphthol red, monoazo red, polyazo red and the like, organic orange pigments such as benzimidazolone orange and the like, organic yellow pigments such as monoazo yellow, disazo yellow, polyazo yellow, benzimidazolone yellow, isoindolinone yellow and the like, organic brown pigments such as benzimidazolone brown, sepia and the like, organic blue pigments such as phthalocyanine blue and the like, organic green pigments such as phthalocyanine green and the like, organic purple pigments such as dioxazine violet, quinacridone violet and the like, and organic black pigments such as aniline black.

Respective Manufacturing Processes (1) Primer Application Process

In the primer application process, primer is applied to the outer circumference of the superelastic alloy wire or the synthetic resin coated superelastic alloy wire (this wire is referred to below as a primer-coated wire). Furthermore, when primer is applied to the superelastic alloy wire or the synthetic resin coated superelastic alloy wire, by regulating the viscosity of the primer liquid, it is possible to control the primer thickness when the superelastic alloy wire is withdrawn from the primer liquid at a constant rate of speed after the superelastic alloy wire is immersed. Further, the thickness of primer in this case is preferably in the range of 1-10 μm. More preferable is for the thickness to be in the range of 2-5 μm. Moreover, it is acceptable for inorganic powders such as metal, ceramic or the like or fluororesin powder to be added to the primer liquid. If this is done, it is possible as mentioned below to form microscopic protuberances in the surface of the fluororesin layer of the fluororesin-coated wire, and to further reduce the frictional resistance with the inner wall of the catheter. Furthermore, it is acceptable to use a pigment-containing primer that is a primer liquid that contains a pigment. With pigment being contained in the primer liquid, it will not be necessary for the fluororesin mentioned below to contain a pigment. In addition, if a pigment-containing primer and a pigment-containing fluororesin are used in the primer liquid application process and the fluororesin application process, the thickness of the pigment-containing layer can become thicker, and it can conceal the backing with a vivid color being easily brought out.

(2) Colored Fluororesin Application Method

In the colored fluororesin application method, a pigment-containing fluororesin dispersion, a fluororesin enamel liquid that contains a pigment, a pigment-containing fluororesin powder body or the like is applied to a primer-coated wire. Furthermore, if a pigment-containing fluororesin dispersion or a fluororesin enamel liquid that contains a pigment is applied to the primer-coated wire, by regulating the viscosity of the pigment-containing fluororesin dispersion or a fluororesin enamel liquid that contains a pigment, it is possible to control the thickness of the pigment-containing fluororesin if the primer-coated wire is withdrawn from the pigment-containing fluororesin dispersion or a fluororesin enamel liquid that contains a pigment at a constant rate of speed after the primer-coated wire has been immersed. Thereafter, the pigment-containing fluororesin dispersion or a fluororesin enamel liquid that contains a pigment on the primer-coated wire is dried, and a pigment-containing fluororesin layer is formed on the primer-coated wire (this wire is referred to below as a pigment-containing fluororesin-coated wire). Additionally, when a pigment-containing primer has been used in the aforementioned primer application process, it is not necessary for the fluororesin to contain a pigment. In addition, if a pigment-containing primer and a pigment-containing fluororesin are used in the primer liquid application process and the fluororesin application process, the thickness of the pigment-containing layer can become thicker, and it can conceal the backing with a vivid color being easily brought out. In addition, if a pigment-containing powder body is applied to the primer-coated wire, the thickness of the fluororesin can be controlled if a suitable particle size is selected for the fluororesin powder body. Furthermore, this thickness of the pigment-containing fluororesin is preferably in the range 1-50 μm, and is preferably thinner than the thickness of the synthetic resin layer. If the thickness of the pigment-containing fluororesin layer exceeds 50 μm, the rigidity of the fluororesin will exert an effect on the flexibility of the wire, and moreover if the thickness is ≦1 μm, sufficient sliding characteristics and durability will not be obtained. Additionally, the layer with a thickness of 5-30 μm is more preferred. In addition, the layer with a thickness of 5-20 μm is further preferred. Moreover, it is acceptable for inorganic powders such as metal, ceramic or the like or fluororesin powder to be added to the pigment-containing fluororesin dispersion or fluororesin enamel liquid that contains a pigment. If this is done, it is possible to form microscopic protuberances in the surface of the fluororesin layer, and to further reduce the frictional resistance with the inner wall of the catheter. Additionally, in the present invention, it is also possible to use dyes without exceeding the scope of the present invention.

(3) Colored Fluororesin Baking Process

In the colored fluororesin baking process, the pigment-containing fluororesin-coated wire is passed into a tunnel furnace that comprises a quartz heater, and the pigment-containing fluororesin that constitutes the outermost layer of the pigment-containing fluororesin-coated wired is heated and baked. Furthermore, in this case, it is preferred to use the quartz heater that can irradiate infrared radiation with a peak wavelength of 1.5-5.6 μm (middle infrared region). In addition, the use of the quartz heater that can irradiate infrared radiation with a peak wavelength of 0.9-1.6 μm (near infrared region) is further preferred.

Furthermore, while it is preferable for the abovementioned primer application process, colored fluororesin application process and colored fluororesin baking process to be carried out continuously, it is acceptable for them to be carried out in batch mode.

Further, while a guide wire was manufactured using the abovementioned method for manufacturing that relates to the present invention, this manufacturing method that relates to the present invention can also be used for manufacturing a catheter or other medical devices. If this is done, it is possible to obtain the same effect.

EXAMPLES

The present invention is further explained below in concrete terms using various Examples.

First Example

After a Ni—Ti (Ni: 49-51 atom %) superelastic alloy wire with a diameter of 0.35 mm was immersed in a fluororesin primer liquid (solid fraction concentration: 35 wt %) (DuPont Co. tradename: 855-300) at 23° C. with the viscosity regulated at 110 cP (centipoise), it was withdrawn at a constant rate of speed and then dried at 150° C. This resulted in a fluororesin layer with a thickness of approx. 1 μm being formed on the Ni—Ti superelastic alloy wire (this wire is referred to below as a primer-coated wire). Next, after the primer-coated wire was immersed in a PTFE dispersion (DuPont Co. tradename: 855-510) that contains zinc yellow pigment (solid fraction concentration: 50 wt %), it was withdrawn at a constant rate of speed and was then allowed to dry naturally. This resulted in a yellow-colored PTFE resin layer with a thickness of approx. 5 μm being formed on the primer-coated wire (this wire is referred to below as a yellow-colored PTFE resin-coated wire). To continue, the yellow-colored PTFE resin-coated wire was passed into a tunnel furnace that comprises a quartz heater (peak wavelength 3 μm) at a temperature of 350° C. as measured by thermocouple for a period of 10 seconds to bake the yellow-colored PTFE resin (this wire is referred to below as a baked yellow-colored PTFE resin-coated wire). When the color of the baked yellow-colored PTFE resin-coated wire obtained thereby was checked, no discoloration was observed. Moreover, when the yellow-colored PTFE resin layer and the fluororesin primer layer were removed from the thus obtained baked yellow-colored PTFE resin-coated wire and the outer surface of the Ni—Ti superelastic alloy wire was observed, no discoloration of the Ni—Ti superelastic alloy wire was observed. In addition, after the baked yellow-colored PTFE resin-coated wire was wrapped around a pipe of diameter 10 mm and then released, it returned to its original shape without taking on a bending habit. From this fact it was concluded that the superelasticity of the Ni—Ti superelastic alloy wire was maintained.

Second Example

A baked yellow-colored PFA resin-coated wire was manufactured under the same conditions as were used for the first example, except that the PTFE dispersion of the first example was replaced with a PFA dispersion. When the color of the baked yellow-colored PFA resin-coated wire obtained thereby was checked, no discoloration was observed. Additionally, when the yellow-colored PFA resin layer and the fluororesin primer layer were removed from the thus obtained baked yellow-colored PFA resin-coated wire and the outer surface of the Ni—Ti superelastic alloy wire was observed, no discoloration of the Ni—Ti superelastic alloy wire was observed. Moreover, after baked PFA resin-coated wire was wrapped around a pipe of diameter 10 mm and then released, it returned to its original shape without taking on a bending habit. From this fact it was concluded that the superelasticity of the Ni—Ti superelastic alloy wire was maintained.

Third Example

A Ni—Ti (Ni: 49-51 atom %) superelastic alloy wire with a diameter of 0.35 mm, after being immersed in a fluororesin primer liquid (solid fraction concentration: 35 wt %) (DuPont Co. tradename: 855-300) at 23° C. with the viscosity regulated at 110 cP (centipoise), was withdrawn at a constant rate of speed (this wire is referred to below as a primer-coated wire), and then without the fluororesin primer liquid on the primer-coated wire being completely dried, a powder body of zinc yellow pigment-containing PTFE powder (Asahi Glass Co. tradename: L150J (mean particle size: approx. 9 μm)) was applied the primer-coated wire, which was then allowed to dry naturally (this wire is referred to below as a yellow-colored PTFE resin-coated wire). To continue, the yellow-colored PTFE resin-coated wire was passed into a tunnel furnace that comprises a quartz heater (peak wavelength 1 μm) at a temperature of 350° C. as measured by thermocouple for a period of 10 seconds to bake the yellow-colored PTFE resin (this wire is referred to below as a baked yellow-colored PTFE resin-coated wire). When the color of the baked yellow-colored PTFE resin-coated wire obtained thereby was checked, no discoloration was observed. Moreover, when the yellow-colored PTFE resin layer and the fluororesin primer layer were removed from the thus obtained baked yellow-colored PTFE resin-covered wire and the outer surface of the Ni—Ti superelastic alloy wire was observed, no discoloration of the Ni—Ti superelastic alloy wire was observed. In addition, after the baked yellow-colored PTFE resin-coated wire was wrapped around a pipe of diameter 10 mm and then released, it returned to its original shape without taking on a bending habit. From this fact it was concluded that the superelasticity of the Ni—Ti superelastic alloy wire was maintained.

Fourth Example

A pigment-containing primer liquid was prepared by adding polyamidoimide varnish (Hitachi Chemical Co., Ltd., tradename: HPC-1000) and zinc yellow pigment to a PTFE dispersion (Asahi Glass Co. tradename: AD912) so that the polyamidoimide varnish can be 20 wt % and the zinc yellow pigment can be 30 wt of to the total weight. Then, a primer-coated wire was manufactured in the same manner of conditions as in the first example, except that the primer liquid used in the first example was replaced with the pigment-containing primer liquid. Next, except for the zinc yellow pigment-containing PTFE dispersion in the first example being replaced by a PTFE dispersion (Asahi Glass Co. tradename: AD912), the coating and baking of the PTFE resin was carried out under the same conditions used in the first example. When the color of the baked yellow-colored PTFE resin-coated wire obtained thereby was checked, no discoloration was observed. Moreover, when the PTFE resin layer and the yellow-colored fluororesin primer layer were removed from the thus obtained baked yellow-colored PTFE resin-coated wire and the outer surface of the Ni—Ti superelastic alloy wire was observed, no discoloration of the Ni—Ti superelastic alloy wire was observed. Additionally, after the baked yellow-colored PTFE resin-coated wire was wrapped around a pipe of diameter 10 mm and then released, it returned to its original shape without taking on a bending habit. From this fact it was concluded that the superelasticity of the Ni—Ti superelastic alloy wire was maintained.

Fifth Example

With the exception of the PTFE dispersion in fourth example being replaced by a zinc yellow pigment-containing PTFE dispersion, the PTFE resin was coated and baked under the same manner of conditions as for the fourth example. When the color of the baked yellow-colored PTFE resin-coated wire obtained thereby was checked, no discoloration was observed. Moreover, when the yellow-colored PTFE resin layer and the yellow-colored fluororesin primer layer were removed from the thus obtained baked yellow-colored PTFE resin-coated wire and the outer surface of the Ni—Ti superelastic alloy wire was observed, no discoloration of the Ni—Ti superelastic alloy wire was observed. In addition, after the baked yellow-colored PTFE resin-coated wire was wrapped around a pipe of diameter 10 mm and then released, it returned to its original shape without taking on a bending habit. From this fact it was concluded that the superelasticity of the Ni—Ti superelastic alloy wire was maintained.

First Comparative Example

The tunnel furnace in the first example was replaced with a circulating hot air oven with an ambient air temperature of 390° C., and the yellow-colored PTFE resin-coated wire was baked for 30 minutes. When the color of the baked yellow-colored PTFE resin-coated wire obtained thereby was checked, a slight discoloration was observed. Moreover, when the yellow-colored PTFE resin layer and the fluororesin primer layer were removed from the thus obtained baked yellow-colored PTFE resin-coated wire and the outer surface of the Ni—Ti superelastic alloy wire was observed, the Ni—Ti superelastic alloy wire was observed to have undergone a color change to a gold color, which was interpreted as due to oxidation. In addition, after the baked yellow-colored PTFE resin-coated wire was wrapped around a pipe of diameter 10 mm and then released, it did not return to its original shape and had taken on a bending habit. From this fact it was concluded that the superelasticity of the Ni—Ti superelastic alloy wire was impaired.

Second Comparative Example

The PTFE dispersion in the first example was replaced with an FEP dispersion, and further the tunnel furnace in the first example was replaced with a circulating hot air oven with an ambient air temperature of 350° C., and the yellow-colored FEP resin-coated wire was baked for 30 minutes. When the color of the baked yellow-colored FEP resin-coated wire obtained thereby was checked, a slight discoloration was observed. Additionally, when the yellow-colored FEP resin layer and the fluororesin primer layer were removed from the thus obtained baked yellow-colored FEP resin-coated wire and the outer surface of the Ni—Ti superelastic alloy wire was observed, the Ni—Ti superelastic alloy wire was observed to have undergone a color change to a gold color, which was interpreted as due to oxidation. Moreover, after the baked yellow-colored PTFE resin-coated wire was wrapped around a pipe of diameter 10 mm and then released, it had taken on a bending habit and did not return to its original shape. From this fact it was concluded that the superelasticity of the Ni—Ti superelastic alloy wire was impaired.

First Reference Example

A Ni—Ti (Ni: 49-51 atom %) superelastic alloy wire with a diameter of 0.35 mm was passed into a tunnel furnace that comprises a quartz heater (peak wavelength 3 μm) at a temperature of 350° C. as measured by thermocouple for a period of 10 seconds. When the outer surface of the Ni—Ti superelastic alloy wire was observed after passing through the tunnel furnace, no discoloration was observed.

Second Reference Example

A Ni—Ti (Ni: 49-51 atom %) superelastic alloy wire with a diameter of 0.35 mm was allowed to stand in a circulating hot air oven with an ambient air temperature of 350° C. for a period of 30 minutes. When withdrawn from the oven, the Ni—Ti superelastic alloy wire was observed to have undergone a color change to a gold color, which was interpreted as due to oxidation.

INDUSTRIAL APPLICABILITY

The method for manufacturing a medical device that relates to the present invention has exceptional utility in that the elastic modulus of a superelastic alloy wire is maintained when the superelastic alloy wire is coated with a fluororesin. Moreover, the method for the manufacture a medical wire relating to the present invention possesses the characteristics that the superior properties of the fluororesin can be elicited without any fading of the color of the colored substance, and the use of fluororesin as the material for the outermost layer constitutes an extremely effective way to color a medical device.

The invention claimed is:

1. A method for manufacturing a medical wire comprising:
   coating a wire with a coating being either a liquid containing a fluororesin or a powder of fluororesin, and the wire being a super elastic alloy wire or a synthetic resin-coated superelastic wire coated with a synthetic resin other than a synthetic resin containing only fluororesin; and
   irradiating the coating at a wavelength of 0.9 to 5.6 μm of infrared radiation using a quartz heater for a prescribed period of time.

2. The method for manufacturing a medical wire according to claim 1, wherein the prescribed period of time is from 3 to 20 seconds.

3. A method for manufacturing a colored medical device comprising:
   coating an outer surface of a medical device substrate with a coating being either a liquid that contains a fluororesin and a coloring substance or a fluororesin powder body that contains said coloring substance; and
   irradiating the coating at a wavelength of 0.9 to 5.6 μm of infrared radiation for a prescribed period of time.

4. The method for manufacturing a colored medical device according to claim 3, wherein the prescribed period of time is from 3 to 20 seconds.

5. The method for manufacturing a colored medical device according to claim 4, wherein
   the medical device substrate is either a superelastic alloy wire or a superelastic alloy wire coated with a synthetic resin other than a synthetic resin containing only fluororesin.

6. The method for manufacturing a colored medical device according to claim 3, wherein
   the medical device substrate is either a superelastic alloy wire or a superelastic alloy wire coated with a synthetic resin other than a synthetic resin containing only fluororesin.

7. A method for manufacturing a fluororesin-coated colored medical device comprising:
   coating an outer surface of a medical device substrate with a liquid primer that contains a fluororesin and a coloring substance;
   applying another coating to the outer surface of the medical device substrate with either a liquid that contains a fluororesin but does not contain a coloring substance or a fluororesin powder body that does not contain a coloring substance; and
   irradiating the coatings at a prescribed wavelength of infrared radiation for a prescribed period of time.

8. A method for manufacturing a colored medical device comprising:
   applying a first coating to an outer surface of a medical device substrate with a primer liquid that contains a fluororesin and a coloring substance;
   applying a second coating to the outer surface of the medical device substrate, the second coating being either a liquid that contains a fluororesin and a coloring substance or a fluororesin powder body that contains a coloring substance; and
   irradiating the coatings at a prescribed wavelength of infrared radiation for a prescribed period of time.

* * * * *